United States Patent
Lindqvist et al.

(10) Patent No.: US 6,458,115 B1
(45) Date of Patent: *Oct. 1, 2002

(54) METHOD, APPARATUS AND ARTICLE RELATING TO A HOOK AND LOOP FASTENING SYSTEM

(75) Inventors: Bengt Lindqvist, London (GB); Roland Pfeifer, Bondues (FR)

(73) Assignee: SCA Hygiene Products AB, Gothenburg (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 87 days.

(21) Appl. No.: 09/284,061
(22) PCT Filed: Sep. 26, 1997
(86) PCT No.: PCT/SE97/01622
§ 371 (c)(1), (2), (4) Date: Jul. 13, 1999
(87) PCT Pub. No.: WO98/15248
PCT Pub. Date: Apr. 16, 1998

(30) Foreign Application Priority Data

Oct. 7, 1996 (SE) .............................. 96036397

(51) Int. Cl.⁷ ................................................ A61F 13/62
(52) U.S. Cl. ............................. 604/391; 24/442; 24/450
(58) Field of Search ..................... 24/442, 450; 604/391

(56) References Cited

U.S. PATENT DOCUMENTS

| | | | |
|---|---|---|---|
| 3,261,069 | * 7/1966 | Mathison | 24/204 |
| 3,370,818 | * 2/1968 | Perr | 248/205 |
| 3,917,254 | * 11/1975 | Watrous | 156/219 |
| 4,519,596 | * 5/1985 | Johnson et al. | 270/32 |
| 4,633,565 | * 1/1987 | DeWoskin | 29/417 |
| 4,853,070 | * 8/1989 | Erb et al. | 156/436 |
| 4,909,870 | * 3/1990 | Gould et al. | 156/66 |
| 4,973,326 | 11/1990 | Wood et al. | |
| 4,980,003 | * 12/1990 | Erb et al. | 156/73.2 |
| 5,256,231 | * 10/1993 | Gorman et al. | 156/178 |
| 5,383,872 | 1/1995 | Roessler et al. | |
| 5,681,302 | * 10/1997 | Melbye et al. | 604/373 |
| 5,961,761 | * 10/1999 | Heindel et al. | 156/163 |
| 6,027,485 | * 2/2000 | Matsushita et al. | 604/391 |
| 6,296,629 | * 10/2001 | Siebers et al. | 604/391 |

FOREIGN PATENT DOCUMENTS

| | | |
|---|---|---|
| EP | 0 324 578 | 7/1989 |
| GB | 2 257 895 | 1/1993 |

* cited by examiner

*Primary Examiner*—Aaron J. Lewis
*Assistant Examiner*—Michael Bogart
(74) *Attorney, Agent, or Firm*—Young & Thompson

(57) ABSTRACT

A method and apparatus for maintaining a fastening tab (20) of a hook and loop fastener system in a storage position on an article, such as a disposable diaper (10). The fastening tab (20) has a first end portion (122) for permanent attachment to the article and a distal end portion (126) provided with projecting hook members (30). The distal end portion (126), in a ready position of the fastening tab, stands free from the article. The distal end portion, in the storage position, contacts a surface of the article. The method includes the steps of attaching the first end portion (122) of the fastening tab (20) to the article, and folding the distal end portion (126) of the fastening tab over the first end portion (122) of the tab such that the hook members (30) contact the surface of the article. In order to improve the contact between the hook members and the article, the hook members (30) of the distal end portion (126) of the fastening tab and the surface of the article are subjected to a relative displacement in a direction substancially parallel to the surface of the article.

12 Claims, 8 Drawing Sheets

METHOD, APPARATUS AND ARTICLE RELATING TO A HOOK AND LOOP FASTENING SYSTEM

TECHNICAL FIELD

The present invention relates to a method of maintaining a fastening member of a hook and loop fastener system in a storage position on an article. The invention further relates to apparatus for carrying out the method.

BACKGROUND OF THE INVENTION

Various fastener systems have been employed on inexpensive or disposable articles such as diapers, including lengths of pressure-sensitive adhesive coated tape, snaps, and hook and loop fasteners. Due in part to the susceptibility of adhesive coated tape to contamination by e.g. talcum powder or baby oil, diapers equipped with hook and loop fastener systems now occupy a growing share of the market.

Different types of hook and loop fastener systems are known. In this respect, reference is made to EP-A-0 491 347, EP-A-0 324 578 and EP-A-0 276 970. Common to these systems is the provision of a fastening tab normally attached to a first waist portion of a diaper, the fastening tab being provided with a region of hook material, and a receiving zone normally on a second waist portion of the diaper, the receiving zone having a plurality of loops to be engaged by the hooks. The fastening tab is commonly a flexible elongate rectangular strip of polymeric material, a first end portion of which is attached to the diaper. The region of hook material is located at a distal end portion of the tab and this distal end portion of the tab extends beyond the edge of the diaper to allow the first waist portion of the diaper to be placed around a wearer and secured to the second waist portion to thereby maintain the diaper in place on the wearer.

A disposable diaper generally comprises a liquid impermeable backsheet, a liquid permeable topsheet, and an absorbent core sandwiched between the topsheet and backsheet. For improved fit and comfort, disposable diapers may also have elasticated leg cuffs and elasticated waist portions. The production process for disposable diapers is highly automated, with constituent materials being supplied to the production line and finished products leaving the production line already packaged for delivery to the consumer. As with all production line processes, faulty batches and stoppages must be avoided.

Hook and loop fastener systems are applied to partially completed diapers as the diapers proceed along the production line. In order to prevent the fastening tabs of the hook and loop fastener system from fouling machinery as the diapers proceed along the production line, it is important that the tabs be maintained in a storage position in which the distal end portion of the tab is folded over the first end portion to thereby preferably contact the topsheet of the diaper. This storage position should be maintained throughout the passage of the diaper along the production line so that the diaper is folded and packaged with the tabs in the storage position. In this manner, when the consumer opens the package, he/she is presented with neatly folded diapers with no visibly protruding tabs.

Although many diapers nowadays have topsheets made from nonwoven material which, to a certain extent, presents loops with which the hooks of the fastening tabs can engage when the tab is folded over to its stored position, the strength of the engagement has sometimes been found to be insufficient to guarantee that the tabs will maintain this storage position during the passage of the diaper along the production line. As a consequence, due to their resilience, the tabs may spring open and snag in machinery of the production line, thereby possibly resulting in production stoppage and/or waste due to the occurrence of faulty products.

In the above-mentioned EP-A-0 324 578, this problem is partially solved by providing a tab with a layer of pressure sensitive adhesive along its central portion such that the central portion of the tab can adhere to the portion of the tab which is permanently attached to the diaper when the tab is in a storage position.

A further conceivable solution to this problem could be to provide the topsheet of the diaper with a patch of loop material adjacent the first end portion of the tab such that the distal end portion of the tab carrying the hooks could engage the patch of loop material in the storage position. Such a solution would however imply higher costs due to the need for additional loop material.

SUMMARY OF THE INVENTION

It is therefore an object of the present invention to provide an alternative method of maintaining a fastening tab or member of a hook and loop fastener system in a storage position, which method avoids the drawbacks associated with other methods.

Since the claimed method ensures improved engagement between the surface of the article and the hook members, existing components of the diaper can be utilized for this purpose without the need for additional means such as adhesive or extra loop material.

It is a further object to provide apparatus for carrying out the method according to the invention.

It is yet another object of the invention to provide a diaper which displays improved properties with regard to maintenance of the storage position of its fastening members.

Preferred embodiments of the method and apparatus are detailed in the respective dependent claims.

BRIEF DESCRIPTION OF THE DRAWINGS

The invention will be described in greater detail in the following, by way of example only and with Preference to the attached drawings in which.

DETAILED DESCRIPTION OF PREFERRED EMBODIMENTS

Although in the following the method according to the present invention will be described in relation to disposable diapers, it is to be understood that the claimed method may be practised on any article which is provided with a hook and loop fastening system. More particularly, the method is eminently suitable for use with disposable articles such as winged sanitary napkins having hook and loop fasteners on the wings, adult incontinence garments and openable-and-reclosable pant diapers.

Figure 1:
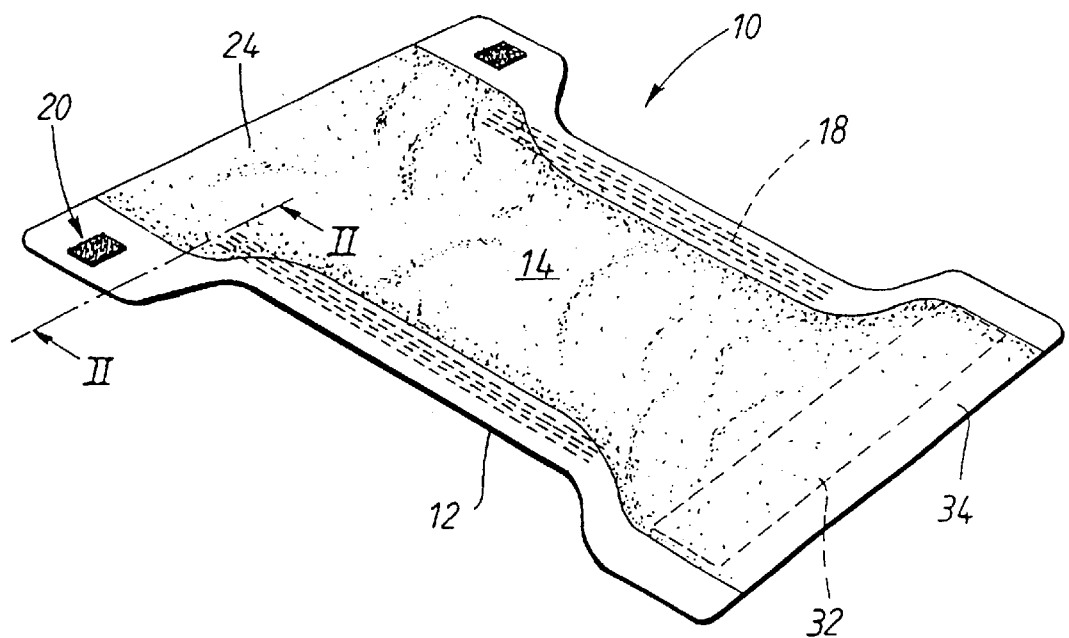
FIG. 1 is a schematic perspective view of a diaper provided with a first embodiment of a hook and loop fastener system.
Figure 2:
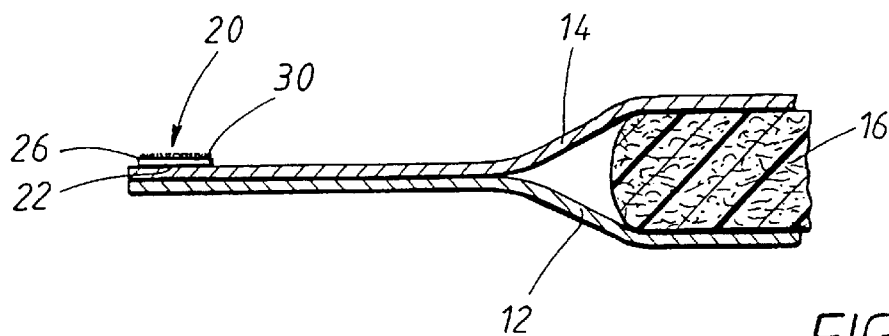
FIG. 2 is a schematic cross-sectional view along line II—II of FIG. 1.
Figure 3:
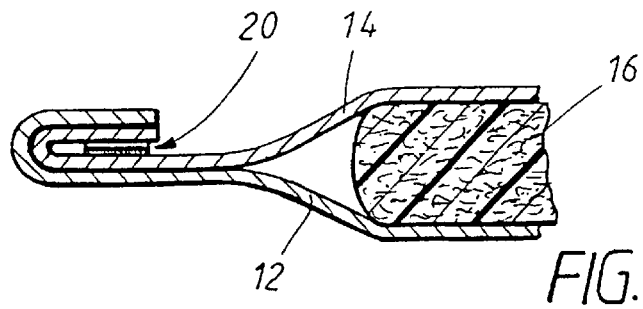
FIG. 3 is a view corresponding to FIG. 2, though with the fastening member in a storage position.

Referring to FIGS. 1 to 3, a diaper is shown generally designated by reference numeral 10. The diaper 10 generally comprises a liquid impermeable backsheet 12, a liquid permeable topsheet 14 and an absorbent core 16 therebetween. The diaper may also incorporate leg elastic 18 disposed along side margins of the diaper. The materials of the constituents of the diaper may be any which are commonly used in this field. For example, the backsheet 12 may be a polyethylene film, whilst the topsheet may be manufactured from a wide range of materials, such as natural fibres, synthetic fibres or a combination thereof. Important is only that the material of the topsheet displays fibres which may be engaged by hooks of a hook and loop fastener system. A material which is well suited for this purpose is spunbond polypropylene nonwoven fabric, though the actual choice of material will be dependent on the type and configuration of the hook members 20 employed in the hook and loop fastener system.

A first embodiment of a typical hook and loop fastener system which may be used in the method according to the present invention includes a pair of polymeric fastening members, generally denoted by reference numeral 20, having a first surface or portion 22 attached to a first waist portion 24 of the diaper 10. As is most clearly shown in FIG. 2, each member 20 has a second surface or portion 26 from which a plurality of hook members 30 project. The hook members 30 are adapted to engage with a loop fastener portion 32 positioned on the outer surface of the backsheet 12 in a second waist portion 34 of the diaper. Typically, in use, the second waist portion 34 of the diaper rests against the abdomen of the wearer, whilst the first waist portion 24 extends over the wearer's back. Naturally, should the outer surface of the backsheet be such that it permits the hook members 30 to engage therewith with sufficient retention force, then there is no need to provide the diaper with additional loop fastener portions 32.

The hook members 30 can be of any suitable material and have any size, shape and distribution density which will allow secure fastening of the fastening tabs to the loop fastener portions 32. For example, the hook members can be made of nylon material in hook- or mushroom-shaped form. A suitable hook fastener is that sold by 3M™ under the identification code CS200.

As shown in FIGS. 2 and 3, the first portion 22 of the fastening member 20 is permanently attached to the topsheet 14 of the diaper, for example by a suitable adhesive or weld.

In FIG. 3 the fastening member 20 is shown in a storage position, i.e. that position which is desired to be adopted when the diaper 10 passes along the production line and which the fastening member retains when the diaper is packaged. In the storage position, a region of the topsheet 14 containing the fastener member 20 is folded over on itself so that the hook members 30 projecting from the second portion 26 of the fastening member contact the outer surface of the topsheet 14.

In accordance with the present invention, once the hook members of the fastening member have come into contact with the outer surface of the topsheet 14, the hook members of the second portion and the surface of the topsheet are caused to effect a relative displacement in a direction substantially parallel to the surface of the topsheet. It has surprisingly been found that by subjecting these parts to a relative displacement, a significantly increased retention force between the hook members 30 and the outer surface of the topsheet 14 is obtained compared to the retention force obtained when no relative displacement takes place. In this respect, the expression "retention force" includes peel resistance and the shear stress resistance. A desirable value of the retention force is one which is capable of maintaining the fastening member 20 in its storage position during passage of the article along the production line and during packaging of the article, though which is not necessarily as high as the retention force between the hook and loop components of a conventional hook and loop fastener.

Without being bound to any specific theory or mechanism, it is believed that the relative displacement of the hook members and the surface of the article in a direction substantially parallel to the surface of the article causes the hook members to "jiggle" between the fibres and loops of the surface material and become snagged thereon.

Before describing apparatus suitable for performing the method according to the present invention, a second embodiment of a fastener system for use on an article will be described with reference to FIGS. 4 to 6. In these drawings, parts corresponding to like parts in FIGS. 1 to 3 are denoted by like reference numerals.

Thus, the hook and loop fastener system of the second embodiment which may be used in the method according to the present invention includes a pair of fastening members, generally denoted by reference numeral 20, in the form of flexible elongate rectangular polymeric fastening tabs made for example from a nonwoven material. Each tab has a first portion in the form of a first end portion 122 attached to a first waist portion 24 of the diaper 19. As is most clearly shown in FIG. 5, each tab 20 has a second portion in the form of a distal end portion 126 which, when the diaper is in a ready position, i.e. a position immediately prior to being attached to a wearer, extends beyond the edge of the diaper. The distal end portion 126 of the tab carries a backing 28 from which a plurality of hook members 30 project. As with the diaper according to FIG. 1, the hook members 30 are adapted to engage with a loop fastener portion 32 positioned on the outer surface of the backsheet 12 in a second waist portion 34 of the diaper. Naturally, should the outer surface of the backsheet be such that it permits the hook members 30 to engage therewith with sufficient retention force, then there is no need to provide the diaper with additional loop fastener portions 32.

Figure 5:
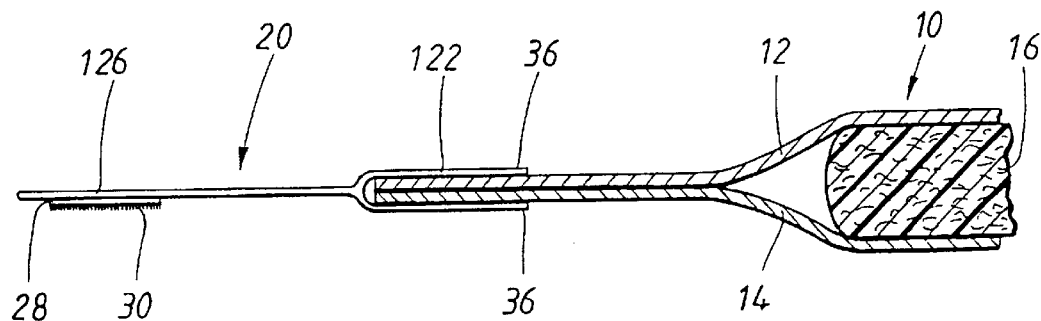
FIG. 5 is a schematic cross-sectional view along line V—V of FIG. 4.
Figure 6:
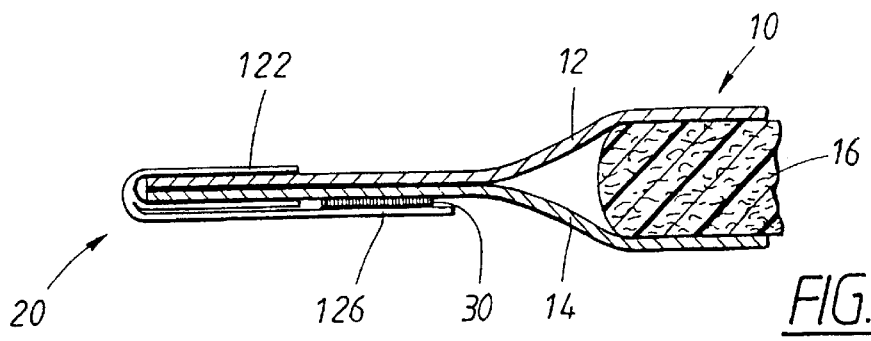
FIG. 6 is a view corresponding to FIG. 5, though with the fastening member in a storage position.

As shown in FIGS. 5 and 6, the first end portion 122 of the tab 20 may be branched into a pair of flaps 36, with one flap being adhered to the outer surface of the backsheet 12 and the other flap being adhered to the outer surface of the topsheet 14. Alternatively, the first end portion of the tab may be unitary and extend between the topsheet and the backsheet.

In FIG. 6, the fastening tab 20 is shown in a storage position, i.e. that position which is desired to be adopted when the diaper 10 passes along the production line and which the fastening tab retains when the diaper is packaged. In the storage position, the distal end portion 126 of the tab is folded over the first end portion 122 so that the hook members 30 projecting from the backing 28 contact the outer surface of the topsheet 14. In accordance with the present invention, once the hook members of the fastening tab have come into contact with the outer surface of the topsheet 14, the distal end portion 126 and the surface of the topsheet are caused to effect a relative displacement in a direction substantially parallel to the surface of the topsheet.

In a further, not-shown embodiment, the invention may be practised on an openable-and-reclosable pant diaper. Such articles generally have a shape corresponding to that of the diaper illustrated in FIGS. 1 and 4, though with the exception that the loop fastener portion 32 forms a part of the topsheet in the second waist portion of the diaper. In other words, the loop fastener portion may be in the form of patches attached to corner regions of the second waist portion or the topsheet itself may serve as such loop fastener portions. The storage position for such a pant diaper is adopted when the fastener members on the first waist portion engage the loop fastener portion or portions in the second waist portion. This storage position then corresponds to the position of use of the pant diaper until the pant diaper is unfastened by separating the first waist portion from the second waist portion.

Common to all embodiments of the invention is that, once in its storage position, the second portion 26, 126 of the fastening member and the surface of the article which contacts the second portion are subjected to a relative displacement in a direction substantially parallel to the surface of the article. In this respect, the expression "surface of the article" means any part of the article which is contacted by the fastening member in its storage position, including any loop fastener member.

Apparatus for performing the method according to the present invention is illustrated in the remaining drawings.

Figure 7:
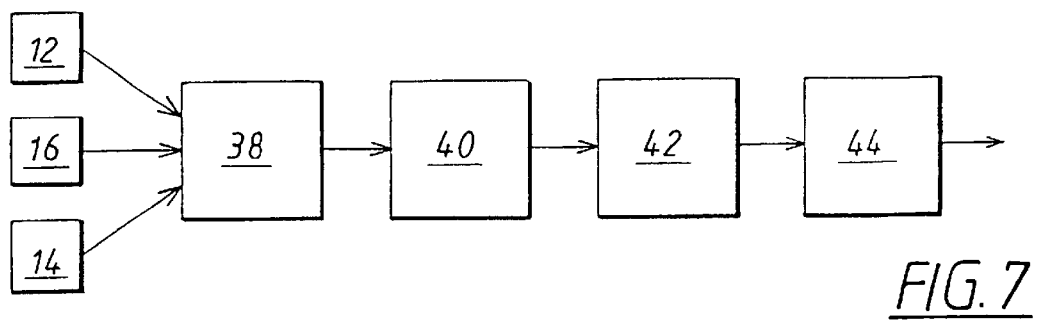
FIG. 7 is a schematic block diagram of a diaper production line incorporating the method according to the present invention.

Accordingly, FIG. 7 schematically illustrates a production line for the production of diapers. Boxes 12, 14 and 16 represent the backsheet, topsheet and absorbent core, respectively, with these constituents being fed to a first station represented by box 38 at which the topsheet and backsheet are adhered together with the absorbent core located therebetween. Thereafter, the partially finished article proceeds to a second station 40 at which the fastening members are applied. With the fastening members in their storage position as shown in FIGS. 3 and 6, the partially finished article proceeds immediately to a third station 42 at which relative displacement of the second portions of the fastening members and the topsheet of the partially finished diaper is performed. Upon completion of the relative displacement, the diaper passes through a fourth station 44 at which subsequent finishing operations are performed. From the fourth station 44 a completed and packaged diaper emerges.

It will be apparent to the skilled person that the above-described sequence of steps may need to be varied, depending on the constituent components of thee product. For example, it is conceivable that the topsheet 14 be provided with fastening members before it is adhered to the backsheet 12 and absorbent core 16. In such a case, steps 40 and 42 will take place before the article passes to the station 38 at which lamination takes place.

Figure 8A:
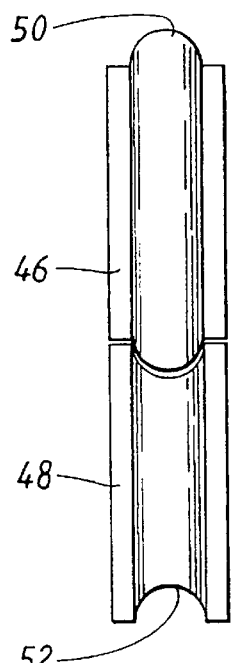
FIG. 8A is a schematic end view of equipment for carrying out the method according to the present invention.
Figure 8B:
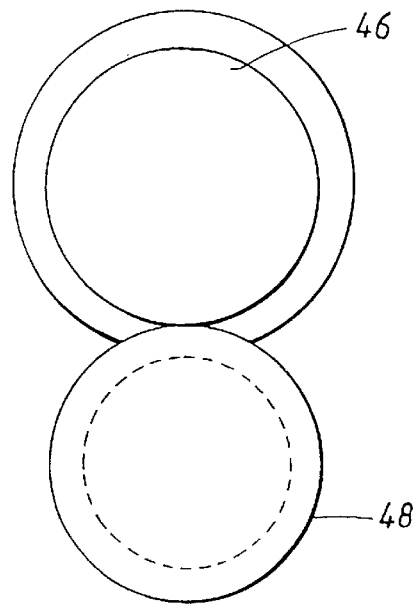
FIG. 8B is a schematic side elevation of the equipment of FIG. 8A.

Means for effecting relative displacement of the distal end portions of the tabs and the surface of the article which the distal end portions contact is schematically illustrated in FIGS. 8A and 8B. Accordingly, the third station 42 (FIG. 7) may be provided with a pair of interengaging rollers, one male roller 46 and one female roller 48, for each side of the article to which fastening tabs 20 are affixed. Thus, for the articles illustrated in FIGS. 1 and 4, the production line will be equipped with two pairs of rollers. In the illustrated embodiment, the male roller 46 has a circumferentially extending protrusion 50 which extends with clearance into a circumferential groove 52 on the female roller 48.

Figure 4:
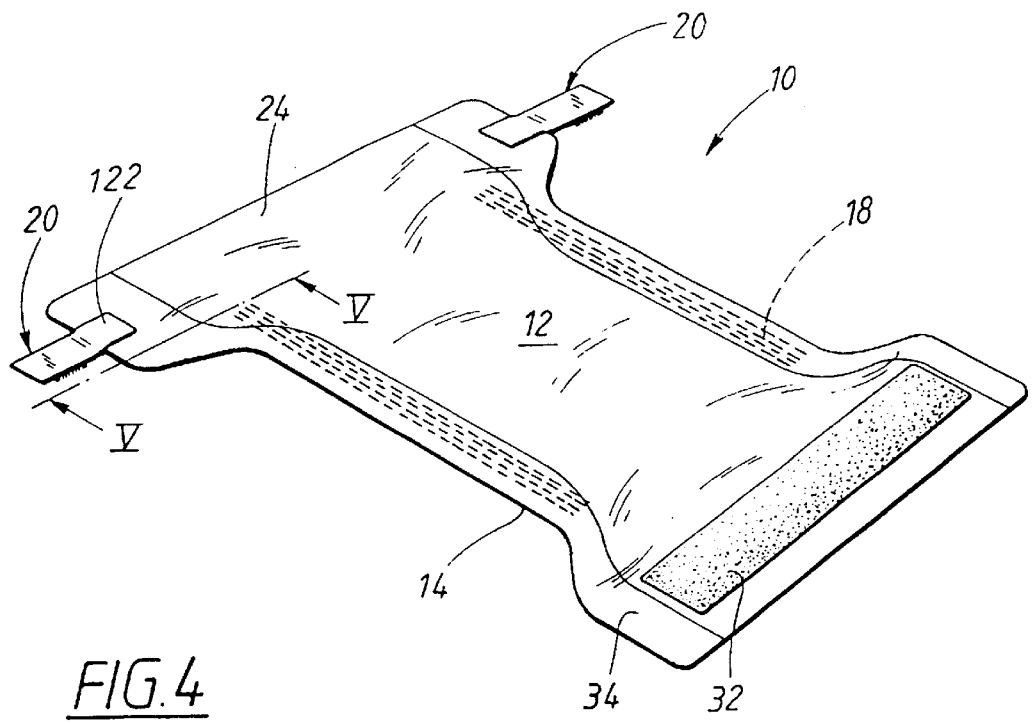
FIG. 4 is a schematic perspective view of a diaper provided with a second embodiment of a hook and loop fastener system.
Figure 9:
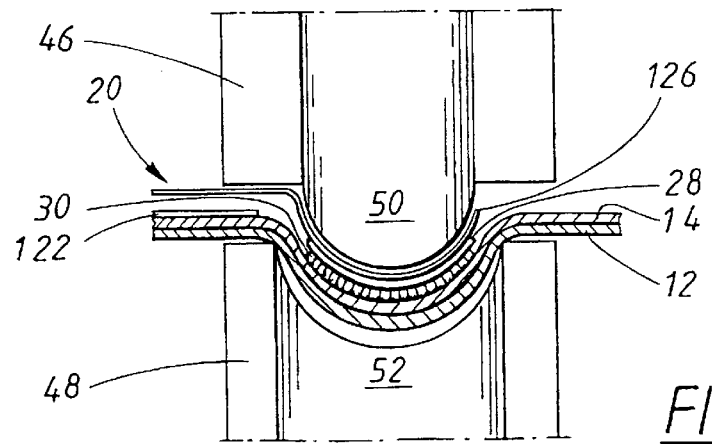
FIG. 9 is a view corresponding to FIG. 8A, though on a larger scale, showing the passage of the diaper of FIG. 4 through the equipment of FIGS. 8A and 8B.

As illustrated in FIG. 9, the clearance between the protrusion 50 and the groove 52 is sufficient to allow the distal end portion 126 of the tab 20 and the laminated topsheet 14 and backsheet 12 of the diaper shown in FIG. 4 to pass therethrough. Relative displacement of the distal end portion 126 of the fastening tab 20 and the outer surface of the topsheet 14 is attained due to the hook members 30 being forced to alter their position relative the loop material of the topsheet as the distal end portion 126 of the fastening tab 20 passes through the pair of rollers. The occurrence of relative displacement will be clearly apparent from a comparison between FIGS. 10A and 10B.

Figure 10A:
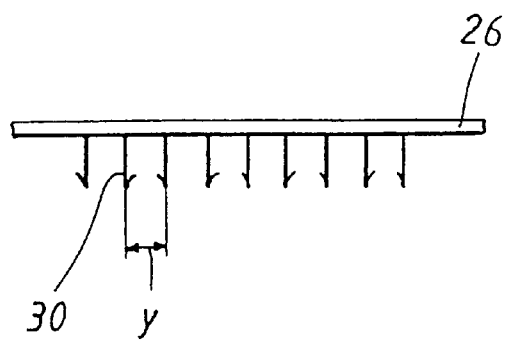
FIG. 10A is a schematic end view of the second portion of a fastening member before being subjected to the method according to the present invention.
Figure 10B:
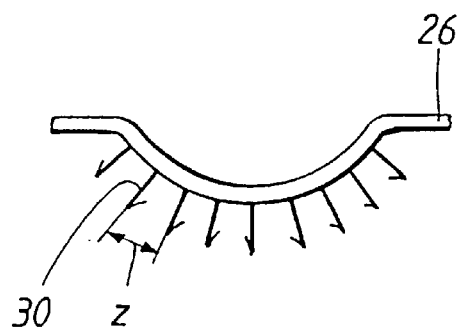
FIG. 10B is a schematic end view of the second portion of a fastening member being subjected to the method according to the present invention.

In FIG. 10A, the second portion 26 of a fastening member is shown in a condition before it is subjected to the method according to the invention in which relative displacement is created. As such, the second portion 26 is generally planar and remote tips of a pair of adjacent hook members 30 provided on the second portion are separated by a certain distance y. When subjected to the method according to the present invention, and as illustrated in FIG. 10B, during displacement of the second portion 26 relative the surface of the article, the distance between the tips of the same adjacent hook members 30 increases to a value z.

Once the fastening member has passed through the station at which relative displacement is effected, the resilience of the fastening member will cause the tips of the hook members to tend, towards each other. This, condition is illustrated in greater detail in FIG. 11.

Figure 11:
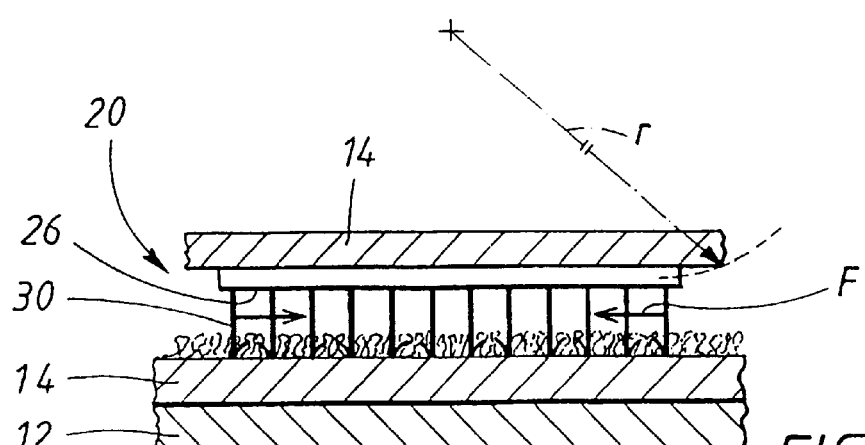
FIG. 11 is a schematic sectional view of the fastening member in its storage position.
Figure 12:
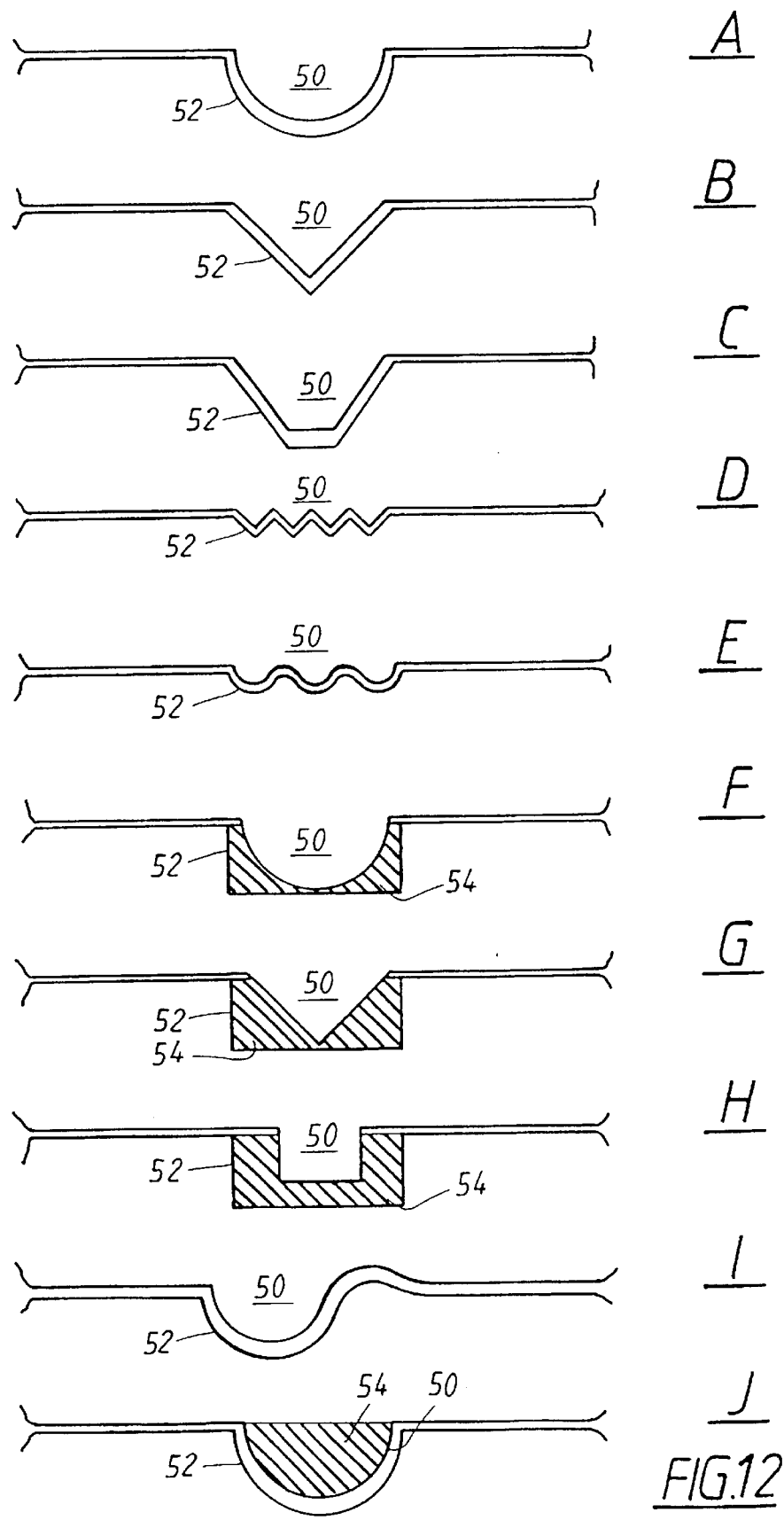
FIGS. 12A to 12L schematically illustrate various possible shapes of rollers for use in the method according to the present invention.
Figure 13:
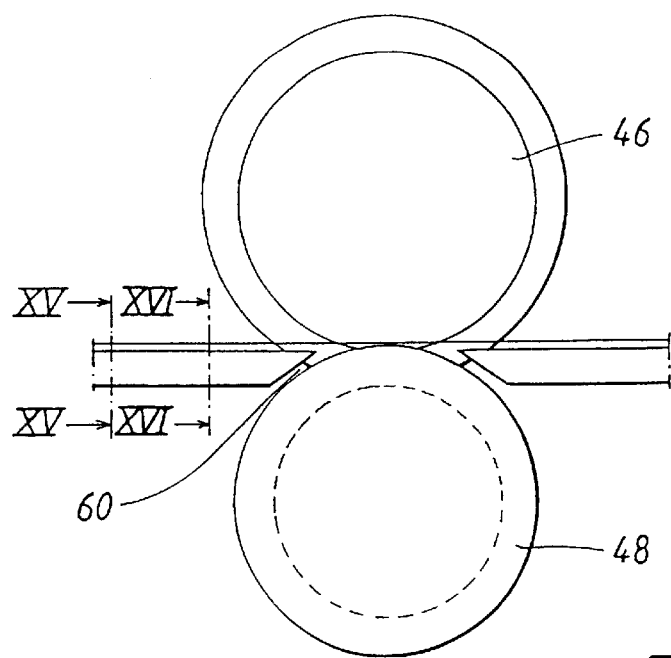
FIG. 13 is a schematic side elevation of a production line incorporating equipment for carrying out the method according to the present invention.
Figure 14:
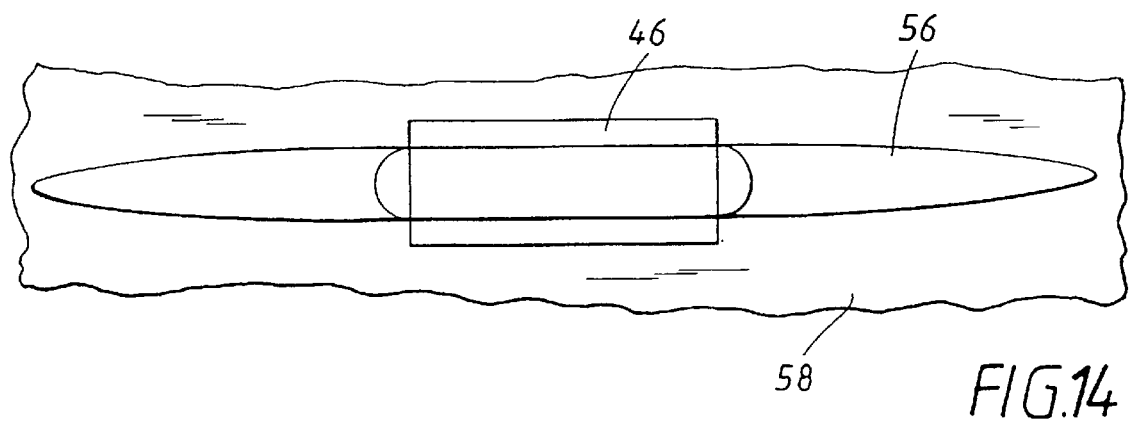
FIG. 14 is a plan view of the equipment shown in FIG. 13.
Figure 15:
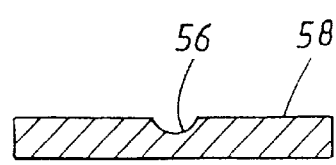
FIG. 15 a schematic cross-sectional view along line XV—XV of FIG. 13.
Figure 16:
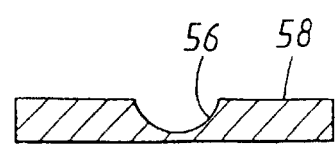
FIG. 16 a schematic cross-sectional view along line XVI—XVI of FIG. 13.

Accordingly, FIG. 11 shows a fastening member 20 in its storage position in which the hook members 30 engage fibres and/or loops of a region of the outer surface of the topsheet 14. Due to the fact that the second portion 26 of the fastening member 20 has previously been subjected to bending to create a radius r in the third station 42, once the second portion leaves the third station land the diaper becomes substantially flat, the hook members 30 of the fastening member will exert compressive forces denoted by the letter F on the region of the surface of the topsheet 14 in directions substantially parallel to the surface. These compressive forces aid in increasing the retention force of the fastening member in the storage position.

The actual size and shape of the interengaging rollers is seemingly not critical. As such, various possible shapes of the interengaging surfaces 50 and 52 are shown by way of example only in FIGS. 12A to 12J. It will be noted that in several of the shown embodiment, rubber 54 or similar resilient material may be placed in the groove 52 or along the protrusion 50. Preferably, the male and female rollers may have a diameter of between 20 and 200 mm, advantageously about 100 mm. The protrusion 50 on the male roller 46 may advantageously have a radial extension of about 6 mm.

A section of one embodiment of the diaper production line at the third station 42 is schematically illustrated in FIGS. 13 to 16 and comprises a pair of interengaging rollers 46, 48 positioned in a mid portion of a guide groove 56 in a table 58 of the production line. The guide groove 56 commences at the upstream side of the pair of rollers 46, 48 and becomes gradually wider and deeper until it reaches the vicinity of the pair of rollers, at which point the table 58 is provided with a through opening 60 within which the pair of rollers interengage. Downstream of the pair of rollers, the shape of the guide groove 56 is a mirror image of the upstream shape. The guide groove 56 serves to guide the second portion of the fastening tab and the portion of the laminate material in contact with the hook members in a properly aligned manner towards and through the pair of rollers 46, 48. The gradual tapering of the downstream portion of the guide groove 56 serves to ensure that the fastening member remains in its storage position once it has passed through the pair of rollers 46, 48.

It will be apparent to the skilled person that important for the method according to the invention is only that the second portion of the fastening member and the topsheet are caused to effect a change in shape to thereby cause the hook members to better engage the material of the topsheet or any other surface of the article which the fastening member is intended to engage in its storage position. In this respect, it will be apparent that [th]e necessary relative displacement of the parts passing through the station 42 may be effected by using a single roller, either male or female, cooperating with a stationary member. Indeed, it is feasible that a suitable relative displacement could be achieved without recourse to rollers by employing a suitably curved projecting plate over which the second portion of the fastening member is made to travel, thereby causing the tips of at least certain of the hook members to spread apart.

Figure 17:
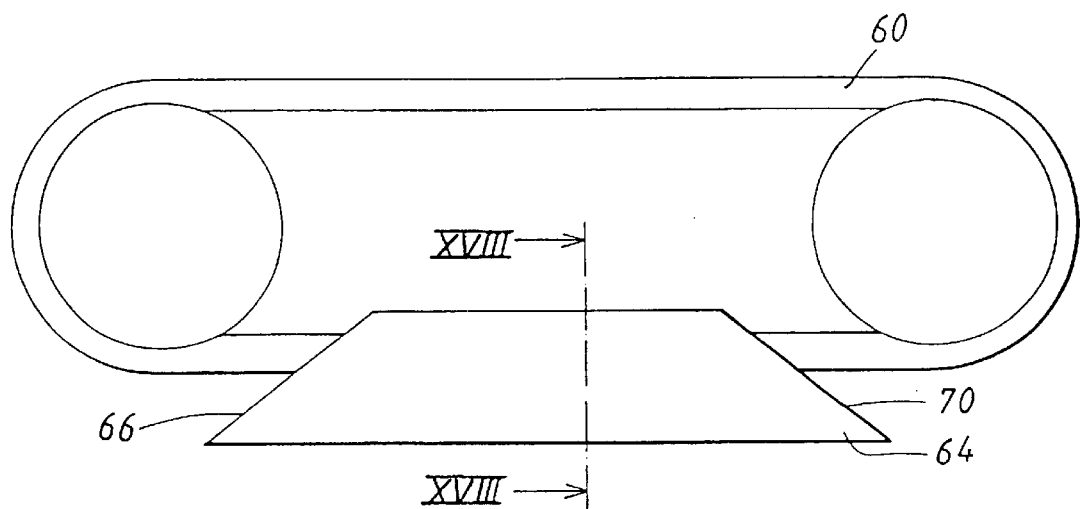
FIG. 17 is a schematic elevational view of an alternative apparatus for carrying out the method.
Figure 18:
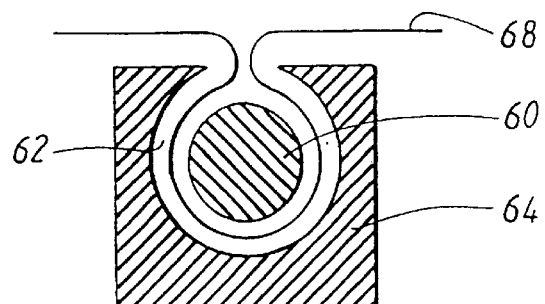
FIG. 18 is a cross-sectional view along line XVIII—XVIII

A further embodiment of apparatus suitable for effecting the relative displacement of the second portion of the fastening member and the material which it contacts is illustrated in FIGS. 17 and 18 and generally comprises a continuous belt 60 which passes through an upwardly open channel 62 in a folding block 64 mounted on the production line table. The belt 60 serves the same function as the male roller 46 in the previously described embodiment, whilst the channel 62 mimics the function of the female roller 48. The folding block 64 has a sloping upstream surface 66 along which the second portion of the fastening member and associated portion of the laminate material run before being drawn into the channel 62 by the belt 60. During passage through the channel 62, the second portion of the fastening member and the laminate material are caused to effect relative displacement to thereby cause the hook members of the fastening tab to enter and engage the surface material of the topsheet. An outline of the fastening member and laminate material within the channel 62 is denoted by reference numeral 68 in FIG. 18. The folding block 64 is provided with a sloping downstream surface 70 to ensure a smooth exit of the fastening member and material from the channel 62.

The above-described embodiment is particularly suitable for practising the method according to the invention on fastening members which are relatively wide. This is because the second portion of the fastening member is caused to adopt a configuration within the folding block 64 in which it covers almost the entire periphery of the belt 60. This can be compared to the male rollers illustrated in FIG. 12 in which the second portion of the fastening member covers only a semi-circle.

Figure 19:
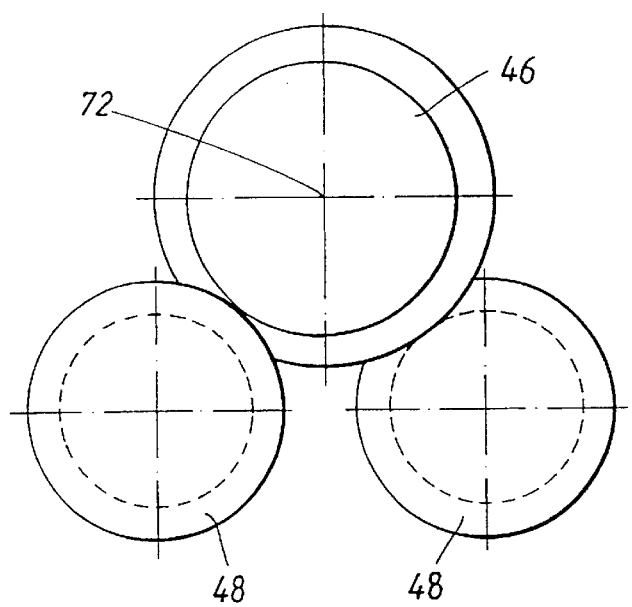
FIG. 19 is a schematic elevational view of an alternative apparatus for carrying out the method.
Figure 20:
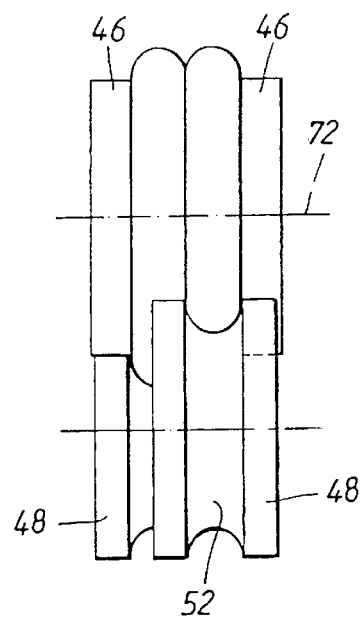
FIG. 20 is a schematic end view of the apparatus according to FIG. 19.

Alternative apparatus for achieving satisfactory relative displacement of the second portion of a relatively wide fastening member and the surface of the article using rollers is illustrated in FIGS. 19 to 22. In FIGS. 19 and 20, a pair of male rollers 46 are arranged adjacent each other on a common axis 72. A first one of these rollers cooperates with a first female roller 48 upstream of the male rollers, whilst the second of the pair of male rollers cooperates with a second female roller 48 downstream of the male rollers. As is apparent from FIG. 20, this arrangement ensures that relative displacement between the second portion of a fastening member and the surface of the article which it contacts can be achieved even if the width of the second portion exceeds that of the groove 52 of one of the female rollers 48.

Figure 21:
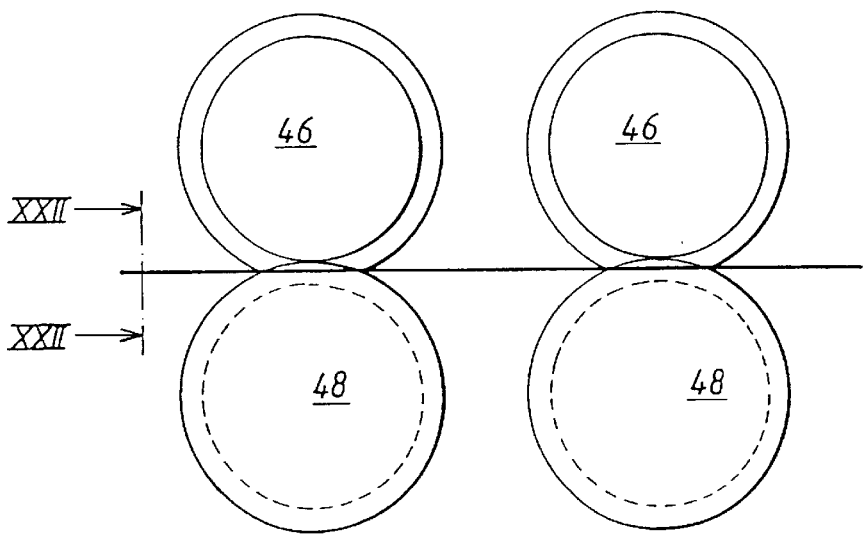
FIG. 21 is a schematic elevational view of further alternative apparatus for carrying out the method.
Figure 22:
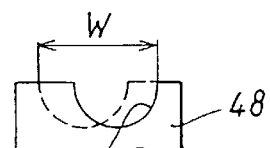
FIG. 22 is a schematic cross-sectional view along line XXII—XXII of FIG. 21.

In the apparatus illustrated in FIGS. 21 and 22, two pairs of cooperating male and female rollers 46, 48 are employed, with one pair being placed upstream relative the other. As is apparent from FIG. 22, the pairs of rollers are axially offset relative each other so that a width w is created within which relative displacement of the fastening member and the surface of the article is achievable this width w being greater than the width of the groove 52 of each female roller 48.

Naturally, the present invention is not restricted to the embodiments described above and shown in the drawings, but may instead be varied within the scope of the appended claims. For example, the pair of rollers 46, 48 need not necessarily be arranged along the longitudinal axis of the diaper. It is further conceivable that two female rollers cooperate with one male roller. The shape of the protrusion 50 need not match that of the groove 52. For example, the protrusion 50 may be rounded whilst the groove 52 has a rectangular cross section. Furthermore, the male roller or rollers may be positioned under the female roller or rollers.

What is claimed is:

1. A method of maintaining a fastening member of a hook and loop fastener system in a storage position on an article, said fastening member comprising a first portion for permanent attachment to said article and a second portion provided with projecting hook members, said hook members of said second portion, in said storage position, contacting a surface of said article, said method comprising the steps of:

attaching said first portion of said fastening member to said article;

bringing said hook members of said second portion of said fastening member into contact with said surface of said article to thereby establish a retention force between said second portion and said surface, the hook members having tips being separated by a first distance, y; and simultaneously displacing parts (a)—said first portion of said fastening member attached to said article, (b)—said second portion of said fastening member, and (c)—said surface of said article that is in contact with said hook members, in a direction that is transverse to said surface of said article, wherein during said displacement said tips of said hooks are separated by a second distance, z, said second distance, z, being greater than the first distance, y.

2. The method as claimed in claim 1, wherein the displacing step comprises the step of causing said parts (a), (b) and (c) to pass a protrusion to thereby effect said displacement.

3. The method as claimed in claim 2, wherein said protrusion is on a male roller.

4. The method as claimed in claim 1, wherein the displacing step comprises the step of passing said parts (a), (b), and (c) through a pair of interengaging rollers.

5. The method as claimed in claim 4, wherein the displacing step comprises the step of passing said parts (a), (b), and (c) along a guide groove upstream and downstream of said pair of rollers.

6. The method as claimed in claim 1, wherein said article is selected from the group consisting of diapers, sanitary napkins, adult incontinence garments and openable-and-recloseable pant diapers.

7. The method as claimed in claim 1, wherein said fastening member is a fastening tab, said first portion of said member is a first end portion of said tab for permanent attachment to said article, said second portion is a distal end portion of said tab provided with projecting hook members, said distal end portion, in a ready position of said fastening tab, stands free from said article and said distal end portion, and in said storage position contacts a surface of said article.

8. A method of maintaining a fastening member of a hook and loop fastener system in a storage position on an article, said fastening member comprising a first portion for permanent attachment to said article and a second portion provided with projecting hook members, said hook members of said second portion, in said storage position, contacting a surface of said article, said method comprising the steps of:

attaching said first portion of said fastening member to said article;

bringing said hook members of said second portion, of said fastening member into contact with said surface of said article to thereby establish a retention force between said second portion and said surface, the hook members having tips being separated by a first distance, y;

subjecting said hook members of said second portion and said surface of said article to a relative displacement in a direction substantially parallel to said surface of said article, wherein during said relative displacement said tips of said hooks are separated by a second distance, z, said second distance, z, being greater than the first distance, y; and passing said second portion of said fastening member and said surface of said article through a pair of interengaging rollers that comprises a male roller having a circumferentially extending protrusion and a female roller having a circumferential groove.

9. The method as claimed in claim 8, wherein either the protrusion or the groove is lined with a resilient material.

10. A method of maintaining a fastening member of a hook and loop fastener system in a storage position on an article, said fastening member comprising a first portion for permanent attachment to said article and a second portion provided with projecting hook members, said hook members of said second portion, in said storage position, contacting a surface of said article, said method comprising the steps of:

attaching said first portion of said fastening member to said article;

bringing said hook members of said second portion of said fastening member into contact with said surface of said article to thereby establish a retention force between said second portion and said surface, the hook members having tips being separated by a first distance, y;

subjecting said hook members of said second portion and said surface of said article to a relative displacement in a direction substantially parallel to said surface of said article, wherein during said relative displacement said tips of said hooks are separated by a second distance, z, said second distance, z, being greater than the first distance, y; and passing said second portion of said fastening member and said surface of said article through an upwardly open channel in a folding block.

11. The method as claimed in claim 10, further comprising the step of passing a continuous belt along said channel such that said second portion of said fastening member and said surface of said article pass between said belt and walls of said channel.

12. Apparatus for maintaining a fastening member of a hook and loop fastener system in a storage position on an article, said fastening member comprising a first portion for permanent attachment to said article and a second portion provided with projecting hook members, said hook members of said second portion, in said storage position, contacting a surface of said article, said apparatus comprising:

a first station at which the fastening member is applied to the article such that the hook members contact the surface of said article, the hook members having tips being separated by a first distance, y; and a second station at which said hook members and said surface of said article are caused to effect a relative displacement in a direction substantially parallel to said surface of said article, wherein said tips of said hooks are separated by a second distance, z, during said relative displacement, said second distance, z, being greater than the first distance, y, wherein said second station comprises a folding block having an upwardly open channel along which a continuous belt passes, such that said second portion of said fastening member and said surface of said article pass between said belt and walls of said channel.

* * * * *